US009691167B1

(12) United States Patent
Frenkel et al.

(10) Patent No.: US 9,691,167 B1
(45) Date of Patent: Jun. 27, 2017

(54) SYSTEMS, APPARATUS AND METHODS FOR COLLECTING AND STORING RAW SCAN DATA AND SOFTWARE FOR PERFORMING DATA PROCESSING, IMAGE RECONSTRUCTION AND INTERPRETATION

(71) Applicants: University of Central Florida Research Foundation, Inc., Orlando, FL (US); iTomography Corporation, Barker, TX (US)

(72) Inventors: Michael Frenkel, Barker, TX (US); Alexander Katsevich, Oviedo, FL (US); Igor Frenkel, Barker, TX (US)

(73) Assignees: University of Central Florida Research Foundation, Inc., Orlando, FL (US); iTomography Corporation, Barker, TX (US)

( * ) Notice: Subject to any disclaimer, the term of this patent is extended or adjusted under 35 U.S.C. 154(b) by 6 days.

(21) Appl. No.: 14/839,377

(22) Filed: Aug. 28, 2015

Related U.S. Application Data

(62) Division of application No. 13/797,457, filed on Mar. 12, 2013, now Pat. No. 9,235,889.

(60) Provisional application No. 61/658,406, filed on Jun. 11, 2012.

(51) Int. Cl.
*G06T 11/00* (2006.01)
*G06T 7/00* (2017.01)
*G06T 1/60* (2006.01)

(52) U.S. Cl.
CPC .............. *G06T 11/005* (2013.01); *G06T 1/60* (2013.01); *G06T 7/0012* (2013.01)

(58) Field of Classification Search
CPC ....... G06T 1/60; G06T 7/0012; G06T 11/005; G06F 17/30244; G06F 19/32; G06F 19/321; G06F 19/3418
See application file for complete search history.

(56) References Cited

U.S. PATENT DOCUMENTS

| 305,061 | A | 9/1884 | Ellis et al. |
| 5,539,800 | A | 7/1996 | Katsevich et al. ............ 378/210 |
| 5,550,892 | A | 8/1996 | Katsevich et al. ............ 370/210 |
| 5,717,211 | A | 2/1998 | Katsevich ................ 250/363.04 |
| 6,574,299 | B1 | 6/2003 | Katsevich ........................ 378/15 |
| 6,771,733 | B2 | 8/2004 | Katsevich .......................... 378/4 |

(Continued)

OTHER PUBLICATIONS

Katsevich. Improved Cone Beam Local Tomography. Inverse Problems. 2006. vol. 22: 627-643.

(Continued)

*Primary Examiner* — Andrew W Johns
(74) *Attorney, Agent, or Firm* — Molly L. Sauter; Smith & Hopen, P.A.

(57) ABSTRACT

Systems, apparatus and methods for collecting, storing, processing, reconstructing, and interpreting raw scan data from a medical diagnostic imaging scan. Raw data after a scan such as a Computed Tomography (CT) scan is sent to a raw scan database system and image reconstruction system, where image volumes are reconstructed using software from the software bank and sent to a data management system. Raw scan data generated once by a scanner is continuously used at later times to reconstruct images of the patient without having to perform additional patient scans.

27 Claims, 6 Drawing Sheets

(56) References Cited

U.S. PATENT DOCUMENTS

| | | | |
|---|---|---|---|
| 6,804,321 B2 | 10/2004 | Katsevich | 378/4 |
| 6,898,264 B2 | 5/2005 | Katsevich | 378/4 |
| 6,947,581 B1* | 9/2005 | Patel et al. | 382/128 |
| 7,010,079 B2 | 3/2006 | Katsevich | 378/4 |
| 7,145,984 B2 | 12/2006 | Nishide | 378/99.5 |
| 7,197,105 B2 | 3/2007 | Katsevich et al. | 378/4 |
| 7,242,749 B2 | 7/2007 | Hsieh et al. | 378/150 |
| 7,436,924 B2* | 10/2008 | Takahashi et al. | 378/4 |
| 7,590,216 B2 | 9/2009 | Katsevich | 378/4 |
| 7,599,534 B2 | 10/2009 | Krishnan | 382/128 |
| 7,672,491 B2 | 3/2010 | Krishnan et al. | 382/128 |
| 7,684,589 B2 | 3/2010 | Nilsen et al. | 382/100 |
| 7,756,314 B2 | 7/2010 | Karau et al. | 382/128 |
| 7,860,286 B2 | 12/2010 | Wang et al. | 382/128 |
| 8,134,571 B2 | 3/2012 | Krishnan et al. | 345/581 |
| 8,195,481 B2 | 6/2012 | Backhaus | 705/2 |
| 8,314,796 B2 | 11/2012 | Pratx et al. | 345/424 |
| 8,396,804 B1 | 3/2013 | Dala et al. | 705/52 |
| 2005/0270025 A1 | 12/2005 | Nozaki et al. | 324/307 |
| 2009/0034790 A1 | 2/2009 | Song et al. | 382/103 |
| 2010/0131887 A1* | 5/2010 | Salazar-Ferrer et al. | 715/788 |
| 2012/0128265 A1 | 5/2012 | Silver et al. | 382/275 |
| 2012/0148125 A1* | 6/2012 | Dekel | 382/128 |
| 2013/0173750 A1* | 7/2013 | Carnevale | 709/218 |

OTHER PUBLICATIONS

Katsevich. Cone Beam Local Tomography. Society for Industrial and Applied Mathematics. 1999. vol. 59 (No. 6): 2224-2246.

Faridani et al. Introduction to Local Tomography. Contemporary Mathematics. 2000: 1-12.

Sato et al. Effect of Radiation Dose and Adaptive Statistical Iterative Reconstruction on Image Quality of Pulmonary Computed Tomography. Jpn J Radiol. 2012. vol. 30: 145-153.

Park et al. Automatic Tube Potential Selection with Tube Current Modulation (APSCM) in Coronary CT Angiography: Comparison of Image Quality and Radiation Dose with Conventional Body Mass Index-Based Protocol. Journal of Cardiovascular Computed Tomography. 2012. vol. 6: 184-190.

Moscariello et al. Coronary CT Angiography: Image Quality Diagnostic Accuracy and Potential for Radiation Dose Reduction Using a Novel Iterative Image Reconstructions Technique—Comparison with Traditional Filtered Back Projection. Eur. Radiol. 2011. vol. 21: 2130-2138.

Raff. Radiation Dose from coronary CT Angiography: Five Year of Progress. Journal of Cardiovascular Computed Tomography. 2010. vol. 4: 365-374.

Katsevich et al. Local Tomography: A New Concept in Computed Tomography Reconstructions. 2011: 1-4.

Louis et al. Contour Reconstructions in 3-D X-Ray Ct. IEEE Transaction on Medical Imaging. 1993. vol. 12 (No. 4): 764-769.

Chen. Local Volume Reconstructions from Width-Truncated Cone-Beam Projections by Convolution Backprojection. Optical Engineering. 2008. vol. 47 (No. 1): 017001-1-017001-10.

* cited by examiner

000
SYSTEMS, APPARATUS AND METHODS FOR COLLECTING AND STORING RAW SCAN DATA AND SOFTWARE FOR PERFORMING DATA PROCESSING, IMAGE RECONSTRUCTION AND INTERPRETATION

CROSS-REFERENCE TO RELATED APPLICATIONS

This invention is a divisional of and claims the benefit of priority to U.S. Non-Provisional patent application Ser. No. 13/797,457, filed Mar. 12, 2013, which claims priority to U.S. Provisional Application Ser. No. 61/658,406 filed Jun. 11, 2012, both of which are incorporated therein by reference in their entirety.

FIELD OF INVENTION

This invention relates to diagnostic imaging, and in particular to systems, apparatus and methods for collecting, storing, and analyzing raw scan data as well as raw scan data processing and image reconstruction algorithms and software used for medical diagnostic imaging, non-destructive material analysis, security and other imaging applications.

BACKGROUND OF THE INVENTION

In the medical industry it is well known to use technologies such as computer tomography (CT), positron emission tomography (PET), magnetic resonance imaging (MRI), ultrasound, conventional X-rays and various other technologies to diagnose the health of a patient. The equipment used to provide such imaging is generally very complex and expensive. For CT imaging, the equipment generally includes a CT scanner that collects raw CT data and proprietary software that reconstructs 3D images out of raw data utilizing scanner's various hardware components, including computers. A computed tomography (CT) method uses X-ray scan data to reconstruct detailed images of a body's interior structure.

Despite the fact that only raw CT data preserves all the medical information acquired during a scan, in practice, only the image data (results of reconstruction) are saved. Once raw data is deleted there is no way back to perform additional image reconstructions without a repeat scan. But, if raw data were saved, radiologists will be able to request retrospective reconstructions to more precisely zero in on specific regions of interest (ROI) without a repeat scan.

In addition, raw data from previous scans can be used for better planning of new scans and much more accurate monitoring of the treatment/disease progress. Availability of raw scan data to a wider group of image reconstruction professionals will also stimulate faster development and adoption of the next generation of reconstruction technologies. The same data sets can be used for testing and improving other new image reconstruction methods.

The saved raw CT data can also be used to more accurately determine the source of a medical problem, optimize treatment or disease monitoring and lead to a paradigm shift in medical imaging, improving medical care not just on the individual patient level but on the entire patient population level.

FIG. 1 shows a conventional prior art workflow of CT data acquisition and image reconstruction using software pre-installed on a scanner.

Referring to FIG. 1, the Scan Order 10 can be generated by a physician to assist with diagnosing or treating a medical issue or related issues. The scanner technician can perform a scan of a patient in accordance with the Scan Order 10 and certain scanner-specific pre-determined scan protocol. The protocol takes into account numerous patient-related variables to optimize diagnostic quality and minimize the amount of radiation exposure by the patient.

During the scan, the scanner 20 collects raw CT scan data, sufficient to perform a computed tomography (CT)-based 3D (three-dimensional) image reconstruction, and stores raw scan data temporarily on the scanner 20 which includes a computer with pre-installed data processing and reconstruction software and temporary CT data storage.

After the scan is complete, the processing and image reconstruction software preinstalled on the scanner 20 performs raw data processing followed by 3D image reconstruction.

The reconstructed 3D image volumes are temporarily stored on the scanner 20 and are also sent to the image repository called Picture Archiving and Communication System (PACS) 30 which also includes a computer for medium-term storage. The PACS 30 system as well as image visualization workstations connected to the PACS 30 can be accessed by physicians/radiologists to read and interpret the reconstructed images of a patient. Long-term storage (e.g., multiple years) of images can also be done.

Prior art exists in the area of image manipulation (or enhancement), which takes place after images have been reconstructed by the scanner system and raw data has been deleted. Such image-based image enhancement has inherent weakness over the raw data-based image reconstruction or raw data-based image enhancement. Many prior art patents in the area of imaging focus on specific algorithms for image manipulation rather than dealing with accumulation and re-inverting (re-imaging) of raw data acquired by a CT scanner/sensors to reconstruct a more accurate image of the body.

Various patents exist that touch on the idea of using previously generated images or downloading CT image data, but only in terms of using the data for their specific algorithm. See for example, U.S. Pat. No. 7,145,984 to Nishide et al.; 7,684I 589 to Nilsen et al.; U.S. Pat. Nos. 7,599,534 and 7,672,491 to Krishnan et al.; 7,7561 314 to Karau et al.; U.S. Pat. No. 7,860,286 to Wang and Jackson; U.S. Pat. No. 8,195,481 to Backhaus; which are each incorporated by reference in their entirety.

Nishide et al. '984 describes a method to plan a scan in consideration of past patient exposures. The method includes a step of sampling information on a patient exposure the subject has received during a scan performed for reconstructing tomographic images, which is appended to each of the reconstructed tomographic images, on the basis of identification information with which the subject is identified; a step of creating a distribution of patient exposures calculated relative to an axis orthogonal to the scanning directions on the basis of the sampled information on the patient exposure (an estimated patient exposure, which is estimated in planning a scan, and an exposure limit); and a step of displaying the created exposure distribution.

The components 10, 20 and 30 of FIG. 1 are generally covered in the above identified patents. Nilsen et al. '589 describes a technique to accelerate the image reconstruction process by dividing one set into subsets, where "The raw image data is decomposed into N subsets of raw image data. N is based on a number of available image generation computer processors. The N subsets of raw image data are processed to create processed image data. The image generation processors perform image processing on the image data in parallel with respect to each other." This patent describes "a method for increasing the performance of a system for processing raw image data via dividing it into smaller subsets of raw image data." This patent would also be potentially obsolete in the future based on continuing advances in efficiency of algorithms and computing power would make this technology unnecessary.

Krishnan et al. '534 and '491 are described as being used for "processing a medical image to automatically identify the anatomy and view from the medical image and automatically assess the diagnostic quality of the medical image. In one aspect a method for automated decision support for medical imaging includes obtaining image data, extracting feature data from the image data, and automatically performing anatomy identification, view identification and/or determining a diagnostic quality of the image data, using the extracted feature data." The methods described here are generally using an Image Database for performing feature analysis, anatomy/view identification and quality assessment of the imaged data (images) but not with raw CT data.

Karau et al. '314 is designed for dealing with imaged data for acquiring images on an imaging system and performing accessing image data with a Computer-Aided Design (CAD) algorithm.

Wang et al. '286 describes a medical image acquisition error detection technique which uses special characteristics of medical images to detect possible errors. In general, the presented technique categorizes medical images based on the type of images. When a medical image is to be examined for possible acquisition errors, it is categorized and a measure of difference between the image and the standard image for the category is computed. If the measure of difference falls outside the acceptable difference for the category, the image is deemed to contain an acquisition error and an alert is issued.

Backhaus '481 describes a teleradiology image processing system to receive, process, and transmit radiology read requests and digital radiology image data. Here, a radiology processing system can include a series of processing components configured to receive digital radiology data from a medical provider, extract relevant information and radiology scan images from the digital radiology data, and initiate and control a workflow with a qualified remote radiologist who ultimately performs a read of the radiology scan images. Other techniques in this patent facilitate data processing within the image processing system in response to medical facility rules and preferences; translation or conversion of digital images to other formats; compilation of patient and medical facility data obtained from the digital radiology data into medical records or data stores; assignment of radiology studies within a teleradiology workflow in response to licensing and credentialing rules; and billing functions in response to completed reads by the remote radiologist.

Thus, the first key problem in the prior art workflows, including solutions currently utilized by the medical industry, is that the raw data are only temporarily stored on the scanner {i.e., a few days) or even deleted right after the image reconstruction process is finished.

Another problem of the current workflow is that the scanner operates like a "black box", where no one except the scanner manufacturer has access to the raw scan data. As such, CT scanners are designed in such a way that it is impossible for anyone except the scanner manufacturer to take the raw data from the scanner to perform an additional image reconstruction with another, potentially superior or more customized, image reconstruction algorithm (software).

It is also impossible for third parties to independently install, potentially superior or more customized, image reconstruction software onto the scanner.

When there is a medical diagnosis needed to further scrutinize a particular target using computed tomography, because raw CT data has been deleted, there is no known reliable alternative which is not based on manipulation with images, but to repeat a CT scan, thereby exposing the patient to additional high doses of X-ray radiation. Not only is this re-image requirement detrimental to the health of the patient, but it requires additional costly system resources, medical personnel time, etc.

Moreover, a repeated scan is often performed on a different scanner, and the image reconstruction is often performed by different software than the one used after the first scan, and the reconstructed images are with different skills, experience, etc.

All these factors can accumulate and result in an inconsistency with the first result and even in an incorrect medical diagnosis. It would be much safer for a patient and more reliable from the medical point of view to resolve a possible issue by returning back to the saved raw data and perform CT reconstruction avoiding all or the majority of the factors mentioned above. On top of that, it would be greatly beneficial to the patients to have an option to perform a repeat reconstruction (of course, without a repeat scan) using the best available reconstruction software. This option is not available in the current art.

These problems not only result in radiation over-exposure of the patient population, but on a global level limit the full potential of medical imaging diagnostic quality and the pace of making available for doctors and patients novel imaging algorithms developed outside the walls of scanner manufacturer technology centers.

Solutions to the above problems are not contemplated by the scanner manufacturers or in the prior art.

Thus, the need exists for a new workflow and system that solve the above problems with the prior art.

SUMMARY OF INVENTION

A primary objective is to provide methods, systems, and apparatus for collecting, storing, and analyzing raw scan data for medical diagnostic imaging, non-destructive material analysis and security applications that can perform image reconstruction of an object even after raw scan data acquired during scanning of this object are deleted from the scanner after the image reconstruction step.

A secondary objective is to provide methods, systems, and apparatus for collecting, testing and storing raw scan data, processing and image reconstruction, and image interpretation algorithms and software for medical diagnostic imaging, non-destructive material analysis and security applications that can be use independently from the software preinstalled on a scanner by the manufacturer of the scanner.

A third objective is to provide systems, apparatus and methods for collecting, storing, and analyzing raw scan data for medical diagnostic imaging and other applications, where the scanner does not operate as a "black box", where only the scanner manufacturer has access to the raw data.

A fourth objective is to provide systems, apparatus and methods for collecting, storing, and analyzing raw scan data for medical diagnostic imaging and other applications, which allows raw scan data from the scanner to be used for performing additional data processing, image reconstruction and interpretation steps with another, potentially superior or more customized, data processing, image reconstruction, and interpretation algorithms (software) developed by a third party.

A fifth objective is to provide systems, apparatus and methods for collecting, storing, and analyzing raw scan data for medical diagnostic imaging and other applications, which allows third parties to independently install, potentially superior or more customized data processing, image reconstruction and image interpretation software onto the scanner or connect a scanner with a third party server capable of performing data processing, image reconstruction, and image interpretation using raw CT data acquired by the scanner but using a third party software.

A sixth objective is to provide systems, apparatus and methods for collecting, storing, and analyzing raw scan data for medical diagnostic imaging and other applications, which allows for additional reconstructions needed to further scrutinize a particular target without exposing the patient to additional high doses of radiation by repeating a CT scan of a patient.

A seventh objective is to provide systems, apparatus and methods for collecting, storing, and analyzing raw scan data for medical diagnostic imaging and other applications, which allows for additional reconstructions needed to further scrutinize a particular target without requiring additional costly system resources such as additional CT scans.

A scanner-independent system for collecting and storing raw scan data of an object or objects and performing raw scan data processing, image reconstruction and reconstructed image interpretation can include a raw scan data transfer module located adjacent to at least one scanner, the raw scan data transfer module to transfer raw data from the at least one scanner onto a raw scan database system after scans are completed and a database for storing raw scan data in compressed or uncompressed formats sufficient for performing image reconstructions at any time after storing raw scan data, an uploading protocol for transferring raw scan data to the raw scan database from any scanner via data networks using a digital information transfer medium; and a data processing and image reconstruction and image interpretation system for providing image processing, image reconstruction and image interpretation from the raw scan data on any stored scan data set at any time.

The at least one scanner can be selected from at least one of: computed tomography (CT) scanner, magnetic resonance imaging (MRI) scanner, positron emission tomography (PET) scanner, an ultrasound scanner, and other types of scanners.

The system can further include the capability to receive via a digital transfer medium any number of additional image reconstruction orders to be performed on the raw scan data stored in the database, which allows the raw scan data to be processed and image reconstructed by the data processing and image reconstruction system to provide additional image reconstructed volumes therefrom, and results of image reconstruction are transferred to one or more external picture archiving and communication system (PACS) data management systems (PACS).

The scan order can be generated based on analysis performed on stored raw data sets on database system, further comprising performing a scan according to the recommended-by-the-system modified scan protocol, with images resulting from the image reconstruction transferred to an external picture archiving and communication system (PACS) data management system.

The raw scan database system can include software providing raw scan data compression and decompression, and computer and software providing capabilities for raw scan and image data storage locally, in a centralized global database, or using cloud computing on the Internet.

The data processing, image reconstruction, and image interpretation system can include software providing raw scan data processing and image reconstruction, software providing interpretation of reconstructed volumes from raw scan data and updating the global raw scan database system with such reconstructed volumes, and an artificial Intelligence software system generating a new scan protocol and optimized data interpretation workflow based on a submitted scan order and the available information on the subject of scan study in the raw scan database system. An example of application of an Artificial Intelligence-based system for improved healthcare is described in U.S. Pat. No. 8,396,804 to Dala et. al., which is incorporated by reference in its entirety.

The digital information transfer medium can be selected from at least one of: a WEB portal, DVD (digital video disc), CD (compact disc), portable drives, and other software carrier transfer medium.

A Software Bank system used with scan data processing, image reconstruction and image interpretation applications, can include a software development and trial system for any raw scan data processing, image reconstruction and interpretation software created by any developers, raw CT (computer tomography) data sets from the raw scan database system and testing procedures for performing trials of any scale of software candidates for the Software Bank, and a Web-enabled portal to apply for a software trial and transfer software modules to satisfy the qualification requirements of the Software Bank.

The software and trial system can include input and output data format standards required to be satisfied by any software applied for a trial, phantom data sets for initial test runs performed by an applicant, software generating a set of real raw scan data from the raw scan database to perform a trial, a queue trial system to manage a number of applicants, required computer power, and data storage volume, and software for an automatic assessment of quality and reliability of software tested during the trial.

Input and output data format standards includes but is not limited to a binary and DICOM formats. DICOM or Digital Imaging and Communications in Medicine is a standard for handling, storing, printing, and transmitting information in medical imaging. It includes a file format definition and a network communications protocol.

Phantom data sets for initial test runs includes but is not limited to only raw scan data of a selected medical phantom or phantoms of simple or human-body-type structures (scan objects).

Queue trial system, which is designed to optimize the use of CPU power and data storage of the trial system, includes but is not limited to a set of scripts automatically managing the trial system.

Software for automatic assessment of quality and reliability of imaging results includes but is not limited to software programs to compare images generated by a tested software program with the phantom structure, if it is tested on a phantom, or with the results of imaging generated by one or a number of previously tested and approved for medical use image software programs.

The software successfully passing through the software development and trial system can be uploaded to the Software Bank and then information about this software becomes available to any user worldwide via a Web-based system.

A method for collecting, storing, processing of raw scan data, and image reconstruction and interpretation used for medical diagnostic imaging for more than one scan order, can include the steps of ordering a scan of a patient with a scanner adapted for diagnosing or treating a medical issue, generating raw scan data collected by the scanner, generating a computer based three-dimensional (3D) reconstructed image using the raw collected data, transferring the reconstructed image to an external picture archiving and communication system (PACS), data management system for providing the reconstructed image, separately storing the raw scanned data generated by the scanner in a raw database storage system, transferring the raw scanned data from the raw database storage system to a data Processing, Image Reconstruction and Interpretation System (PIRIS) and reconstructing additional images at any time with the PIRIS, wherein the raw scanned data is able to be continuously used at later times without having to perform another patient scan.

The scanner type can be selected from at least one of: computed tomography (CT) scanner, magnetic resonance imaging (MRI) scanner, positron emission tomography (PET) scanner, an ultrasound scanner, and other imaging modalities allowing to retrieve raw scan data.

The method can include the steps of ordering a second scan for the same patient, transferring the second scan order to the raw CT (computer tomography) database system with a digital information transfer medium, transferring the raw scan data from the first scan order to the PIRIS, and generating a second image reconstruction order based on the raw scan data generated by the scanner from the first scan order, the second image reconstruction based on reconstructed volumes from the raw scan data, so that the second image reconstruction is sent to the external picture archiving and communication system (PACS) data management system.

The transfer medium being can be selected from at least one of: a WEB portal, DVD (digital video disc)1 CD (compact disc)1 portable drives, and other software carrier transfer medium, The method can include the steps of providing software to the PIRIS from a software bank, for the image volumes to be reconstructed.

In a preferred embodiment that can use a CT scanner, the detector data are subjected to various preprocessing steps such as calibration, scatter correction, beam hardening correction, and the like before it can be used for image reconstruction. For the purposes of this patent application, the raw data (also referred to raw scan data or raw CT data) can mean data at any stage, i.e. before any preprocessing done and all the way up to the stage when all preprocessing is performed and the preprocessed data is ready to be used for image reconstruction.

Further objects and advantages of this invention will be apparent from the following detailed description of the presently preferred embodiments which are illustrated schematically in the accompanying drawings.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

A list of the components in the figures will now be described.

1. Workflow steps of prior art scan order (10), scanner (20) and data management (30).

10. Scan order.

20. Scanner with pre-installed data processing and image reconstruction software and a temporary CT data storage.

30. Data Management—Picture Archiving and Communication System (PACS) or any other image visualization and/or storage platform.

100. Automatic scanner-independent, stand-alone workflow system.

21. Raw CT scan Data Transfer Module (DTM).

105. Raw CT Data.

106. Raw CT data compression software module.

110. Raw CT Database System (RDBS).

111. ROBS request and decompressed raw CT data.

120. Data Processing, Image Reconstruction, and Image Interpretation System (PIRIS).

121. Request to consult with database systems (RDBS) and/or upgrade them.

130. Reconstructed Image Volumes.
200. Workflow of Embodiment 100 with Additional Reconstruction Order without changing scan protocol.
210. Reconstruction Order.
115. Raw CT data decompression.
300. Workflow of Embodiment 200 with Additional reconstruction order and/or changing scan protocol.
310. Reconstruction order and/or protocol change.
400. Workflow of Embodiment 300 Web upload steps.
112. Global Raw CT Database System (GRDBS).
410. CT system Web portal to upload data and software.
415. Uploading of new raw CT data sets onto GRDBS.
417. External special requests to consult with GRDBS.
420. Software Trial and QC systems.
430. Software Bank.
440. Installation of a software module from the software bank onto a scanner.
500. Workflow of Embodiment 400 permitting an external user to request consulting with the GRDBS (i.e., with the global database of raw CT data, processed CT data, and CT imaged data/images) created and constantly expanded using raw CT data from any number of CT scanners.

First Embodiment

Figure 2:
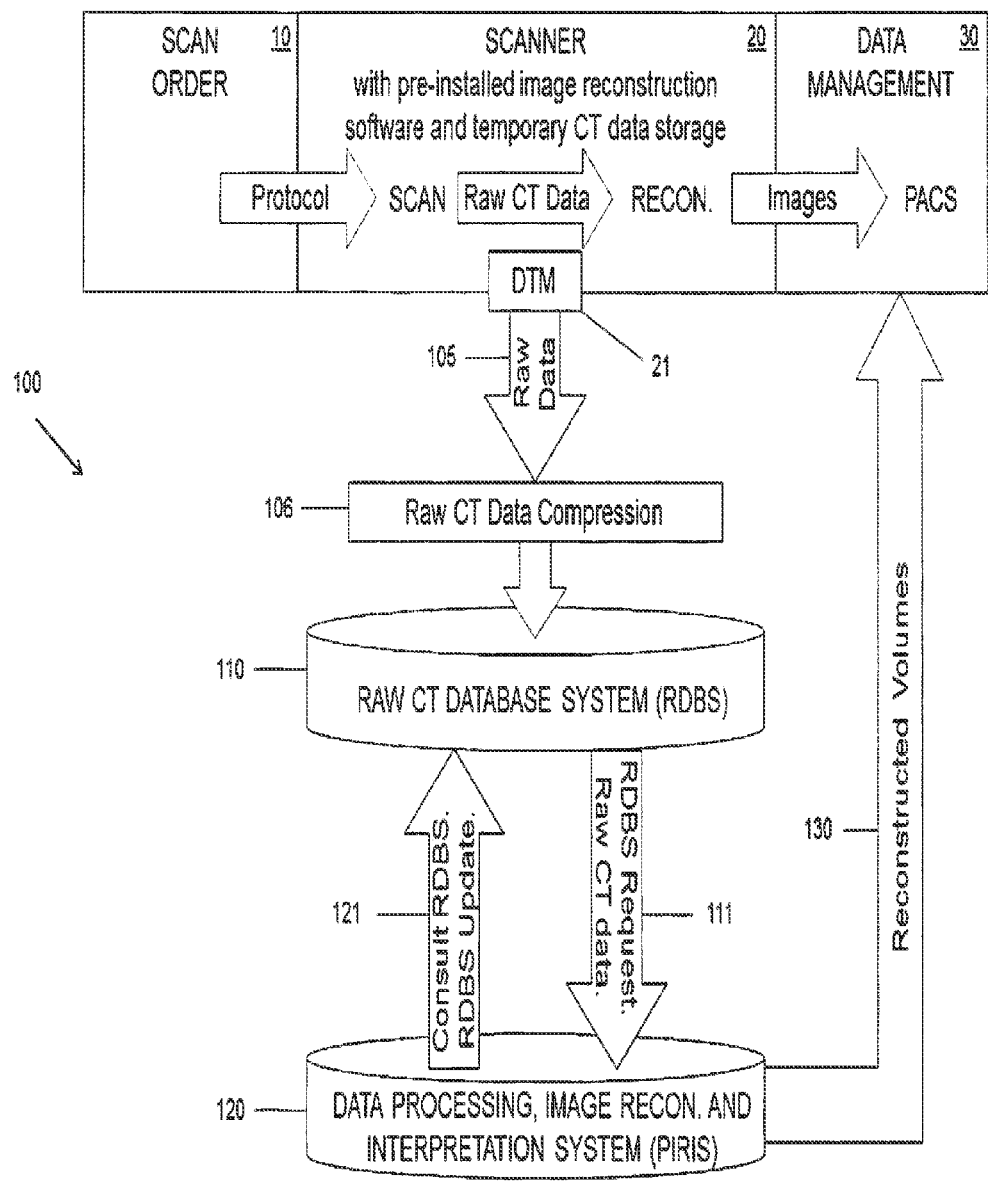
FIG. 2 shows a scanner-independent, stand-alone workflow system providing raw CT scan data-based image reconstruction performed automatically in parallel with the scanner's system, without impacting the operational workflow of the scanner or scan protocol. Raw scan data are stored in the raw CT database system (ROBS) and processes are performed using software from the data Processing, Image Reconstruction and Interpretation System (PIRIS).

FIG. 2 shows a scanner-independent, stand-alone workflow system 100 providing raw CT data image reconstruction in parallel and/or simultaneously with image reconstruction performed by the software preinstalled on the scanner, without impacting the operational workflow of the scanner or scan protocol.

Figure 1:
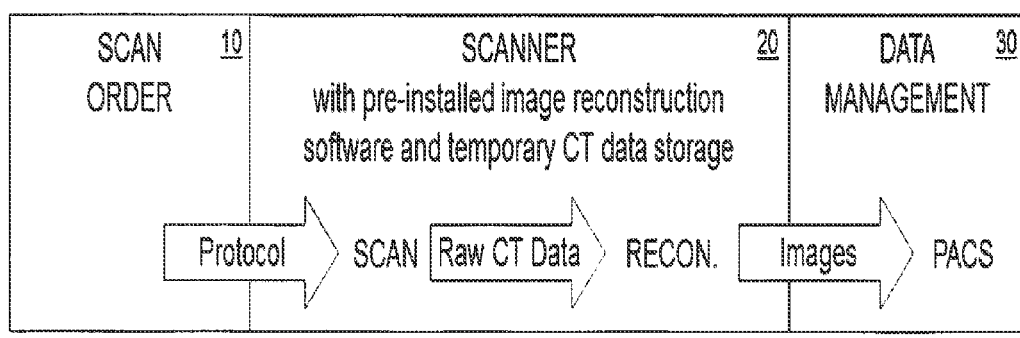
FIG. 1 is a prior art workflow of CT data acquisition and image reconstruction with scanner pre-installed software.

Here, the workflow for raw CT Database System (RDBS) and Data Processing, Image Reconstruction, and Image Interpretation System (PIRIS) use alternative data processing and image reconstruction software modules installed on an external server. This workflow does not require changing a scan protocol and therefore does not require an additional order from a physician generally required in the prior art workflow system of FIG. 1.

Raw CT data are transferred from the scanner 20 using the Data Transfer Module 21, which provides wireless/wire-based data transfer from the CT scanner 20 to the ROBS 110. During this step raw CT data can be compressed 106 to reduce storage space on the RDBS.

Referring to FIG. 2, there can be the following steps required as described below.

In a first step (1a), Scan Order 10, a physician orders a scan, which includes at least one of: computed tomography (CT), magnetic resonance imaging (MRI), positron emission tomography (PET), ultrasound, and the like, and can be used to assist with diagnosing or treating a medical issue or related issues in a similar manner as referenced in the prior art.

The second step, (2a), includes Setup and Scan 20. The Scan can be performed in accordance with the Scan Order (1a) and a scanner and scan-specific protocol. The scan-specific protocol is based on the initial Scan Order from the physician.

A third step, (3a), can occur in the Raw CT Database System 110. Immediately after the scan is performed or at a later time, the raw CT data are transferred from the scanner 20 using the Data Transfer Module 21. The raw data 105, which includes scanner information, protocol of the scan, and other related patient and scan data acquired before and during the scan and sufficient to perform data processing and image reconstruction, can be automatically compressed (106) to reduce storage space on the RDBS 110 and transmitted to and stored on the Raw CT Database System (ROBS) 110, which includes hardware and database management software for local and/or cloud-based storage and organization of Raw Data.

An example of a system that is partially similar to the "RAW CT DATABASE SYSTEM" 110 that includes the hardware and software for this computer system can be found in at least U.S. Pat. No. 7,436,924 B2 by Takahashi et al., which is incorporated by reference. The U.S. Pat. No. 7,436,924 B2 by Takahashi et al. does not contemplate using the data base for the purposes of giving access to the data to third parties, using the data for later reconstruction by other algorithms, for improving the quality of healthcare by means including but not limited by the monitoring of the treatment of the patient, reducing the number of repeat scans, and the like. Another difference between the present invention and patent U.S. Pat. No. 7,436,924 B2 by Takahashi et al. is connecting the database to the Software Bank that can be used for image reconstruction.

The RDBS (Raw CT Database System) 110 can include, but is not limited to, raw CT data sets, scanner information, de-identified patient information, unique RDBS patient ID to be used to retrieve past CT scans of the patient, other medical information and/or data required to perform image reconstruction at any time without needing any additional information from other sources of information. Raw scan data can be stored in the original uncompressed form or in compressed form. RDBS 110 can also store the original reconstructed volumes generated by pre-installed on the scanner image reconstruction software.

The above set of data and scan information can be fully sufficient and can be stored for an indefinite amount of time. It is assumed that RDBS 110 is being backed-up on a regular basis and access to the system is not allowed to any unauthorized personnel to preserve RDBS integrity and confidentiality.

For the purposes of subsequent use, the database 110 should provide a way to establish a connection between patients' data (for example: raw CT data, reconstructed images, and the like) stored in the database and the patients' personal identifying information. For example, each data set in the database can be given a unique identifying number, and a separate database may contain the collection of these identifying numbers and the corresponding patient personal data such as social security numbers.

The Raw Data 105 can be stored for any period of time, such as but not limited to 7 years or longer, if patients and/or hospitals made special requests and/or paid for an extended storing time.

A fourth step (4a) occurs in the Data Processing, Image Reconstruction, and Image Interpretation System (PIRIS) 120. Raw CT Data 105 can be first compressed (106) and then stored or stored in uncompressed form in the RDBS (110) and then automatically uploaded to the PIRIS System 120, and the required steps as per RDBS request 111, including image reconstruction are performed, utilizing the software pre-installed on the PIRIS System 120. As many data processing, image reconstruction, and data analysis and interpretation runs can be performed as needed, utilizing, for example, various image reconstruction algorithms and other relevant software and input data. If necessary, these runs can all be performed simultaneously. The software on the PIRIS System 120 is regularly updated, tested, and new software modules are added as needed and/or when become available.

An example of a system having some elements partially similar to "DATA PROCESSING, IMAGE RECON AND INTERPRETATION SYSTEM (PIRIS)" 120 can be found in at least U.S. Pat. No. 8,134,571 B2 to Krishnan et al., which is incorporated by reference in its entirety. The significant difference between the present invention and the U.S. Pat. No. 8,134,571 B2 to Krishnan et al. is that the latter is dealing with image processing only, whereas the present invention deals with image reconstruction from raw data. By image processing we mean the manipulation of images that are of diagnostic value by themselves.

Additional step (4b) is a continuation of step (4a) from FIG. 2. A Data Interpretation component is added to the Image Reconstruction System 120 (collectively, "Data Processing, Image Reconstruction and Interpretation System, PIRIS", 120), which can be consulted by the physician in step (1c) to provide data helpful for determining the type of software and protocol to be utilized for the particular patient as well as additional information that can be obtained by utilizing the Raw CT Database and the software on the Image Reconstruction and Interpretation System.

An example of a system that is partially similar to the PIRIS system 120 can be found in U.S. Patent: U.S. Pat. No. 7,436,924 B2 by Takahashi et al. which is incorporated by reference in its entirety. The U.S. Patent U.S. Pat. No. 7,436,924 B2 by Takahashi et al. does not contemplate using the data base for the purposes of giving access to the data to third parties, using the data for later reconstruction by other algorithms, for improving the quality of healthcare by means including but not limited by the monitoring of the treatment of the patient, reducing the number of repeat scans, and the like. Another difference between the present invention and U.S. Pat. No. 7,436,924 B2 by Takahashi et al. is connecting the database to the Software Bank that can be used for image reconstruction.

Raw CT Data Processing, Image Reconstruction, and Interpretation System (PIRIS) 120 can include but are not limited to various algorithms that can be utilized individually or according to a predetermined workflow. In order to be used in the course of medical care, and utilized by the PIRIS system, the individual software modules and workflows are assumed to be tested and passed the FDA and other relevant regulatory approval processes that might be required in the future. Some algorithms, which can be part of PIRIS, are described in the above referenced U.S. patents to at least U.S. Pat. No. 7,436,924 B2 by Takahashi et al. and U.S. Pat. No. 7,684,589 B2 by Nelsen et al., which are incorporated by reference in their entirety.

Other examples of algorithms which can be part of PIRIS are described in U.S. Pat. Nos. 5,539,800; 5,550,892; 5,717,211; 7,590,216 all to Katsevich which cover local tomography, which in their entirety are all incorporated by reference, and U.S. Published Patent Application 2012/0128265 to Silver et al. entitled: Method and System Utilizing Iterative Reconstruction with Adaptive Parameters for Computer Tomography (CT), which is also incorporated by reference in its entirety.

A fifth step (5a) is the storage and transmission of reconstructed images. The image volumes reconstructed in step (4a) are stored on the Raw CT Database System (RDBS) 110, previously described, and are also transmitted to an image repository called Picture Archiving and Communication System (PACS) 30 and/or other visualization workstations or image storage media.

Reconstructed image volumes mean reconstructed 3D structure of an object under study for which a CT scan has been ordered and then raw CT scan data have been acquired and processed. Reconstructed image volumes allow evaluating the whole patient's body or a certain Region of Interest (ROI) of a patient.

The physician is notified immediately (via all possible electronic notifiers) that the images have been reconstructed and are ready to be viewed and analyzed. Electronic notifiers can include but are not limited to automatic email message, text message, telephone call, and the like.

Second Embodiment

Figure 3:
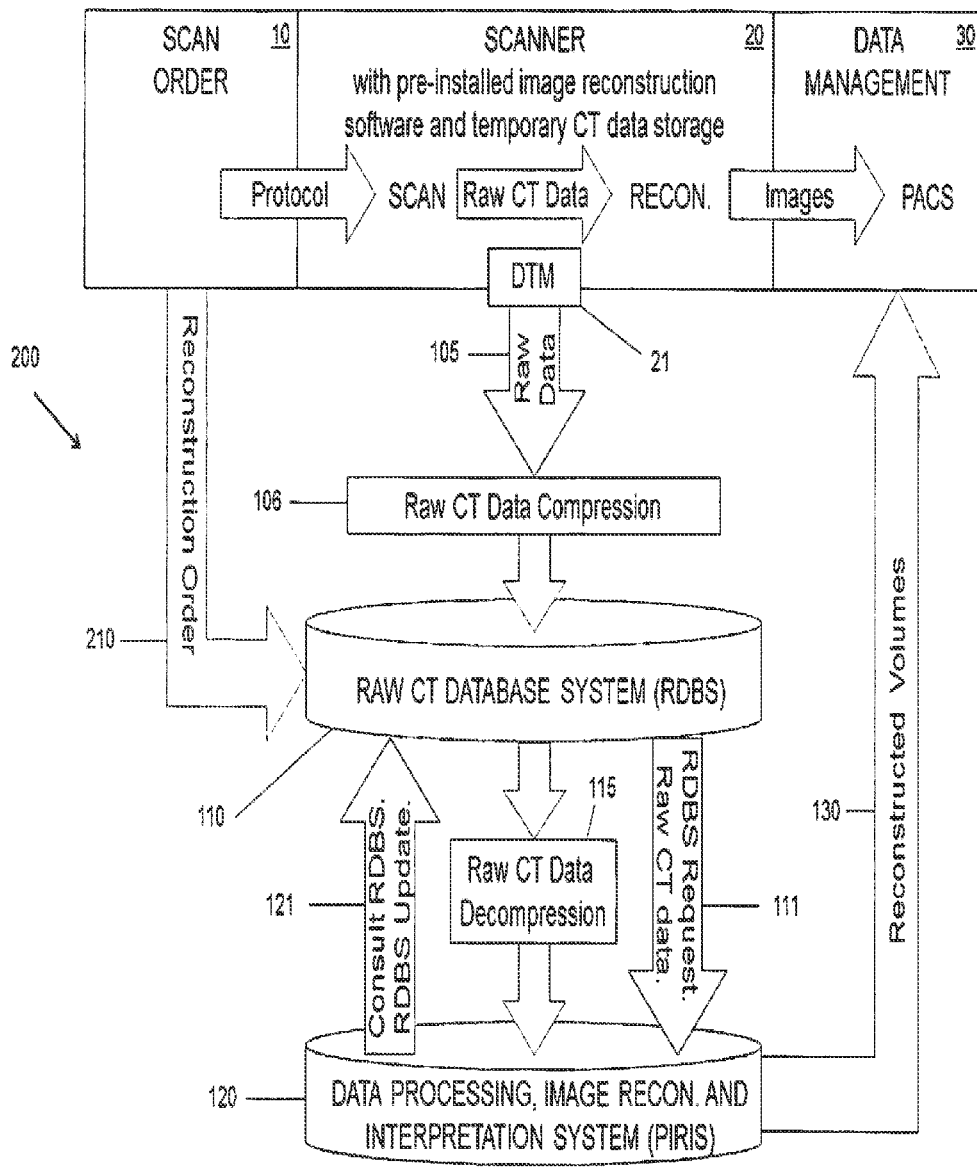
FIG. 3 shows a modified scanner-independent, stand-alone workflow system used in FIG. 2 that also allows a user to select software pre-installed on the data Processing, Image Reconstruction, and Interpretation System (PIRIS) to be ran in parallel with the scanner's system and without changing the conventional operational workflow of the scanner or scan protocol.

FIG. 3 shows the scanner-independent, stand-alone workflow system 200 of FIG. 2 which allows a system user to select the software from the list of pre-installed on the PIRIS System 120 modules, previously described. Here, workflow for RDBS 110 and PIRIS System 120 can use data processing, image reconstruction and interpretation software modules installed on an external server computer.

This workflow does allow applying an alternative scan protocol simultaneously with the protocol utilizing a pre-installed on the scanner image reconstruction software and therefore it requires an additional order from a physician.

Referring to FIG. 3, an additional step (1b) can occur in the Scan Order 10. As a continuation of (1a) from FIG. 2, a physician orders a scan (for example, CT, MRI, PET, ultrasound, and the like) to assist with diagnosing or treating a medical issue or related issues and orders specific software module(s) to be utilized in performing image reconstruction (without impacting the scanner's workflow). This additional Reconstruction Order (see left arrow 210 in FIG. 3) can be ordered at the time of the original scan or at any later date if the Raw Data are saved in the computer system of the Raw CT Database System.

Currently, doctors have to use the software that comes with the scanner, but by using the ROBS and PIRIS systems, physicians will have freedom to choose the best image reconstruction algorithm (software) available at the time of the scan.

Specific software modules can include but are not limited to for example, local tomography to one of the inventors of the subject invention. See for example, U.S. Pat. Nos. 5,539,800; 5,550,892; 5,717,211; 7,590,216 all to Katsevich which cover local tomography, which in their entirety are all incorporated by reference. See for example, U.S. Published Patent Application 2012/0128265 to Silver et al. entitled: Method and System Utilizing Iterative Reconstruction with Adaptive Parameters for Computer Tomography (CT), which is also incorporated by reference in its entirety.

Also, doctors will be able to request retrospective reconstructions to more precisely zero in on specific areas of interest without a repeat scan. Further, raw data from previous scans can be used for better planning of new scans and much more accurate monitoring of the treatment progress or disease development.

Third Embodiment

Figure 4:
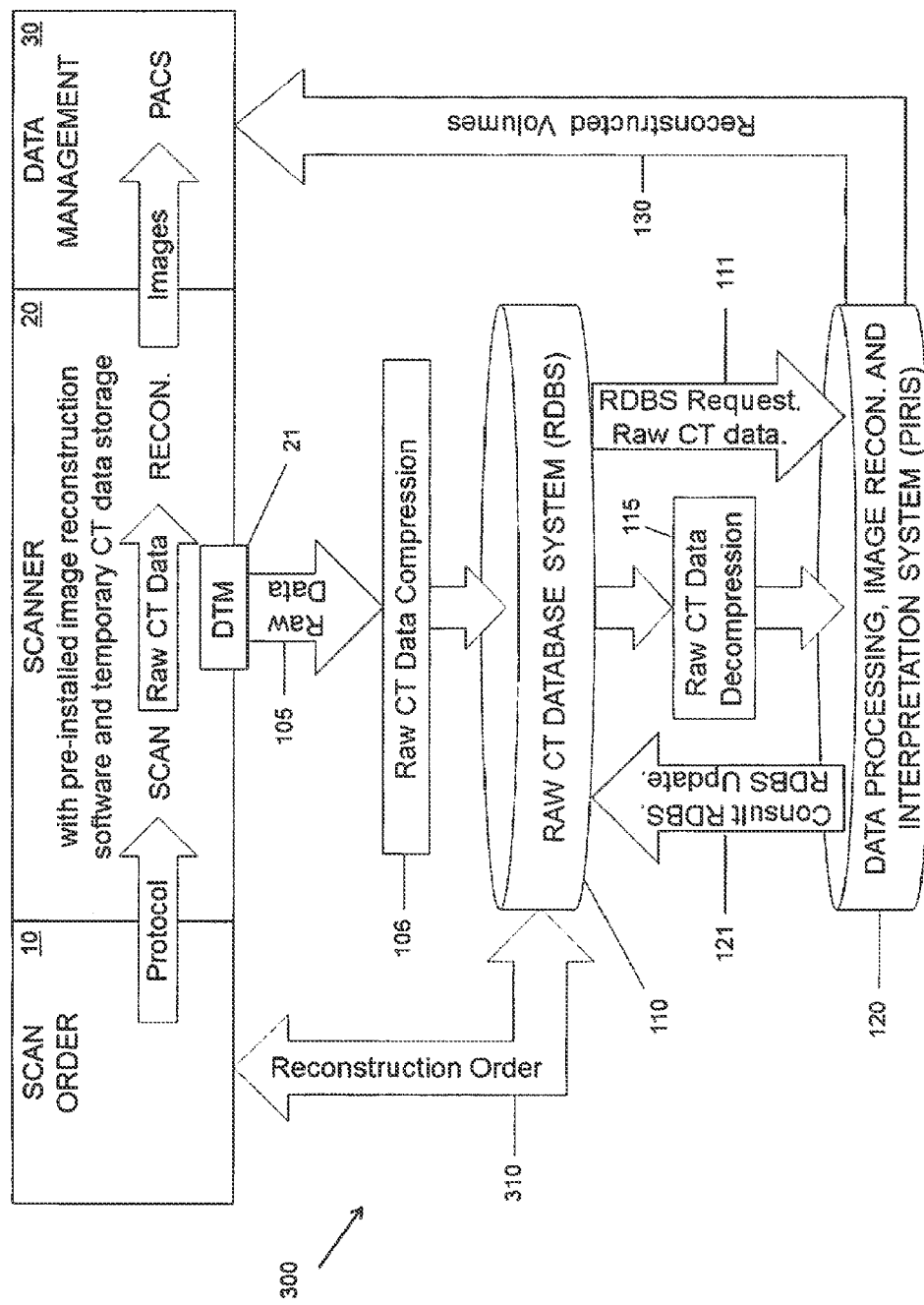
FIG. 4 shows a modified scanner-independent, stand-alone workflow system used in FIG. 3 that also allows a user to select software pre-installed on the data Processing, Image Reconstruction, and Interpretation System with a new scan protocol guiding scan performance.

FIG. 4 shows a modified scanner-independent, stand-alone workflow system 300 used in FIG. 3 that allows a user to select software pre-installed on the computer of the PIRIS System 120 with a new scan protocol guiding scan performance.

Referring to FIG. 4, workflow 300 for the raw CT Database System (RDBS) 110 and PIRIS system 120 uses alternative software installed on an external server and alters the scan protocol and consults with the data analysis expert system of PIRIS.

Additional step (1c) occurs in the Scan Order 10 as a continuation of step (1b) from FIG. 3. Rather than selecting the software pre-installed on the scanner 20 and the related protocol (as shown and described in FIG. 2 and FIG. 3), the physician can elect to modify the scan protocol in accordance with medical requirements to assess patient's medical condition or a treatment and using the additional capability provided by the software in the Software Bank that is not provided by the software on the scanner.

The result can be that the scanner 20 does not perform image reconstruction or that the images reconstructed on the scanner 20 are not of diagnostic quality to investigate a particular medical condition or perform a detailed treatment analysis. The additional step outlined in FIG. 3 which include step (1b) can be applicable here as well.

An example of application of an alternative algorithm can be based on Local Tomography. See for example, U.S. Pat. Nos. 5,539,800; 5,550,892; 5,717,211 7,590,216 all to Katsevich which cover local tomography, which in their entirety are all incorporated by reference.

With superior edge detection, the alternative algorithm provides the potential for enhanced diagnostic accuracy and be applicable to many areas in the body including heart, brain, spine, liver, and lung. Disease detection should be enhanced because of the edge enhancement characteristics of the local tomography algorithm. Moreover, with the full implementation of collimator assisted local scanning, radiation dose can be significantly reduced. This is an example of additional capability that could be provided by software in the software bank. In other words, the physician can elect to use collimators knowing that there is a code in the software bank that can reconstruct a diagnostic-quality image from such a lower radiation CT data set.

Image reconstruction software can be run using CPU (central processing unit) or GPU (graphics processing unit) types of computer processors that are referenced in for example in U.S. Pat. No. 7,684,589 B2 to Nilsen et al.; U.S. Pat. No. 7,145,984 B2 to Nishide; and U.S. Pat. No. 8,314,796 to Pratx, et al; which are all incorporated by reference in their entirety.

Fourth Embodiment

Figure 5:
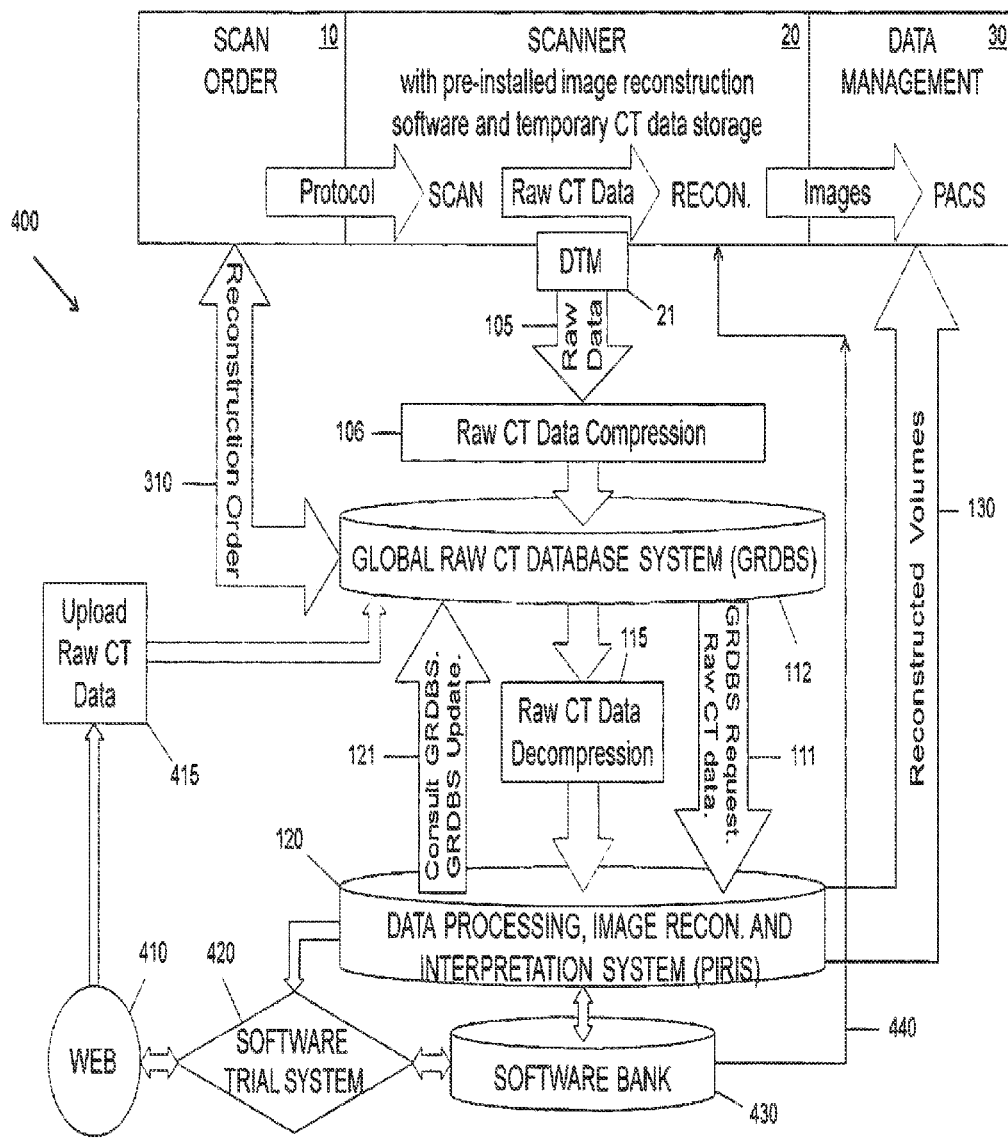
FIG. 5 shows a modified scanner-independent, stand-alone workflow system used in FIG. 4 with an additional web-based option permitting the system administrator controlling the global raw CT scan database system and the Software Bank to test and then install new software onto the software bank. Selected software modules from the software bank can then also be installed onto the scanner. The word global throughout this patent application references that the corresponding database is connected to the Internet.

FIG. 5 shows a modified scanner-independent, stand-alone workflow system 400 used in FIG. 4 with an additional web-based option 410 permitting the user to request a software trial 420 of new software and, if approved, it can be loaded onto the Software Bank 430. Another additional web-based option 415 permitting an external user to upload raw CT data sets via a web portal 410 connected to the Global Raw CT Database System (GRDBS) 112.

Here, the new workflow for global raw CT Database System and Image reconstruction systems 400 uses an alternative software installed on an external server computer. This workflow allows the alteration of a scan protocol via consulting with PIRIS and uses software from the Software Bank 430. Referring to FIG. 5, step 4c allows for the Data Processing, Image Reconstruction and Interpretation System 120 to be connected to a repository of software ("Software Bank") 430.

Software from the Software Bank 430 can be installed on the Data Processing, Image Reconstruction and Interpretation System (PIRIS) 120 as part of previously described step (1b) and step (1c) utilizing a Web portal 410 or by other electronic technique. Other electronic techniques can include but are not limited to software carrier media, e.g., DVD, portable drives, and the like.

Under additional step (6a) prior to being uploaded into the Software Bank 430, software passes through trials utilizing the Raw Data 105 from the GRDBS 112 (collectively, "Software Trial System") 420.

Software from the Software Bank 430 can include but is not limited to local tomography, iterative reconstruction, and other data processing, 3D image reconstruction algorithms. Examples of Local Tomography-based and Iterative Reconstruction algorithms are referenced in, for example, in U.S. Pat. No. 7,590,216 B2, to Katsevich, and U.S. Published Patent Application 2012/0128265 to Silver et al. entitled: Method and System Utilizing Iterative Reconstruction With Adaptive Parameters For Computer Tomography (CT), respectively, which are all incorporated by reference in their entirety.

The software should be required to pass regulatory approval (for example, FDA U.S. Food and Drug Administration) as well as other quality control steps to ensure compliance with system's performance standards. Access to the Software Trial System can be obtained via a Web portal 410 or by other electronic techniques, such as but not limited to software carrier transfer medium, such as but not limited to, DVD (digital video disc), CD (compact disc), portable drives, and the like.

Quality control steps include but are not limited to software testing procedures using predetermined phantom and raw CT data sets from the GRDBS to satisfy pre-determined performance standards that can be based on but not limited to tests for speed and accuracy of data processing, image reconstruction and analysis software.

Alternatively, new software modules can be uploaded from the Software Bank and installed onto the scanner 440.

Regulatory government approval can include but is not limited to FDA (U.S. Food and Drug Administration) approval, and other government approval and the like. The described above part of this embodiment, in which additional software is installed on the scanner, has the advantage of eliminating potential time delays associated with transferring data from the scanner to the database and then to the reconstruction engine.

An Artificial Intelligence (AI) system can also be a part of the computer GRDBS 112, previously described. The AI system preselects the best algorithm based on the type of scan, patient data, and the like, and suggests to the radiologist what additional software might be needed in every particular case. For example, to minimize delay, the reconstruction engine might reconstruct different volumes prior to the physician ordering these reconstructions. Thus, if the physician wants to see several images, they will be instantaneously available. For example, if the AI system knows that the patient is overweight, this means that the CT data are noisier, and therefore the system will run an iterative reconstruction algorithm, which is more stable with respect to noise in the data. Another example of application of an Artificial Intelligence-based system for improved healthcare is described in U.S. Pat. No. 8,396,804 to Dala et. al., which is incorporated by reference in its entirety.

Fifth Embodiment

Figure 6:
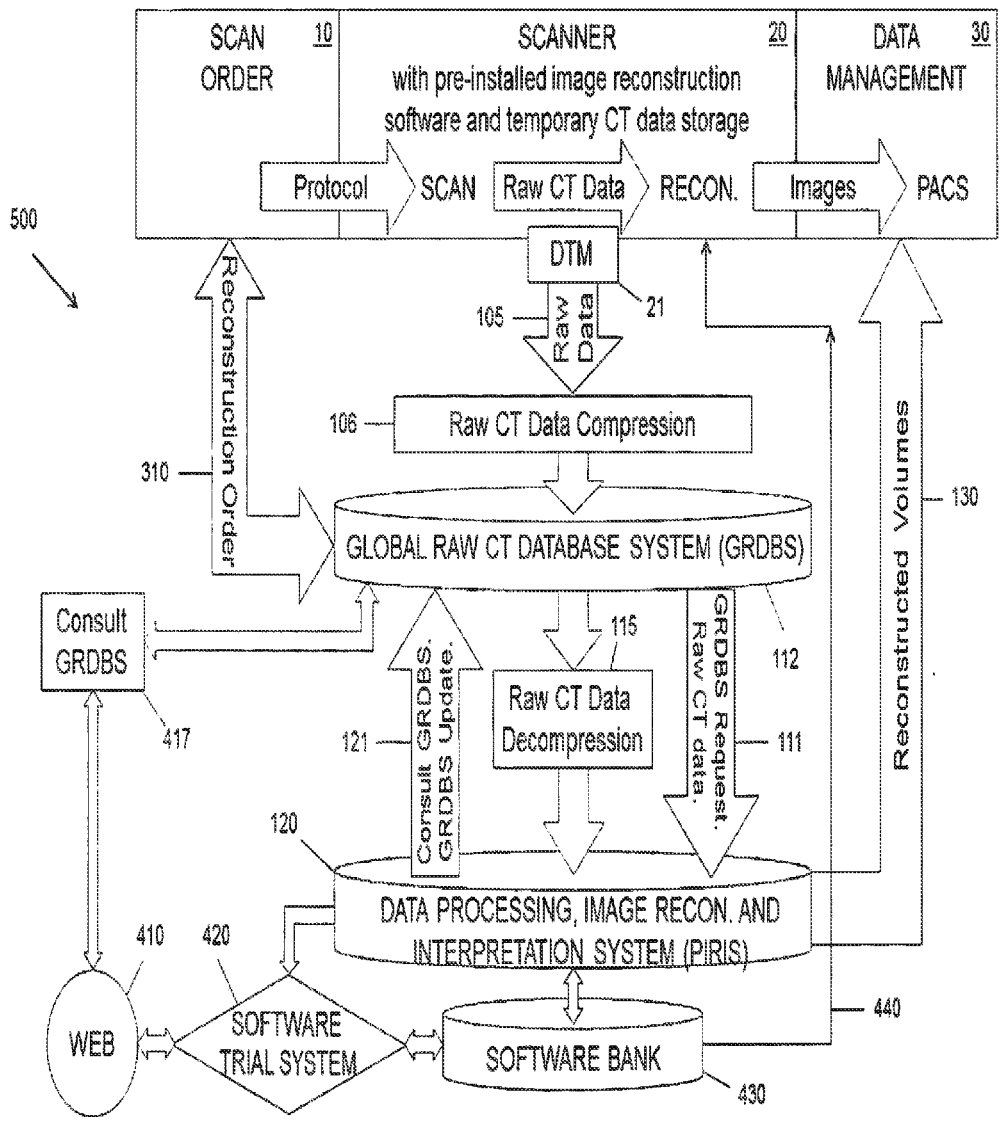
FIG. 6 shows a modified scanner-independent, stand-alone workflow system used in FIG. 5 additional web-based option permitting external users to consult with the global raw CT database system.

FIG. 6 shows a modified scanner-independent, stand-alone workflow system 500 used in FIG. 5 with an additional web-based option 417 permitting an external user to request consulting 112 with the GRDBS (i.e., with the global database of raw CT data, processed CT data, and CT imaged data/images) created and constantly expanded using raw CT data from any number of CT scanners.

Such a consulting with the GRDBS can be used, for example, in the regular course of medical care for improving of treatment, early detecting or predicting of diseases, improving and testing of new reconstruction and/or interpretation methods, selecting of the best method for a specific disease, and the like. To maintain image reconstruction consistency, and therefore providing a more reliable reply on a request from an external user, image reconstructions of a number of raw CT data sets from the GRDBS, which are required to be performed to generate such a reply, can be based on the same (unique) image reconstruction algorithm. Imaging process can be based on a single-type of reconstruction algorithm (For example, a Filtered-Backprojection-type algorithm (FBP)). Examples of these algorithms can be found in at least U.S. U.S. Pat. Nos. 6,574,299; 6,771,733; 6,804,321; 6,898,264; 7,010,079; 7,197,105; 7,242,749 to Hsieh et al; U.S. Pat. Nos. 7,280,632; and 7,305,061 all to Dr. Katsevich and U.S. Pat. No. 7,242,749 to Hsieh et al, that are all incorporated by reference in their entirety.

Additionally image processing can be based on a joint/sequential application of reconstruction algorithms (e.g., Local Tomography and Iterative Reconstruction). See for example, U.S. Pat. Nos. 5,539,800; 5,550,892; 5,717,211; 7,590,216 all to Katsevich which cover local tomography, which are all incorporated by reference in their entirety. See for example, U.S. Published Patent Application 2012/0128265 to Silver et al. entitled: Method and System Utilizing Iterative Reconstruction With Adaptive Parameters For Computer Tomography (CT), which incorporated by reference in its' entirety.

To assess quality of reconstruction, a comparison of two or more reconstructed 3D images of an arbitrary property (not necessarily density, the other one is gradient-like density computed by local tomography, etc.) can be done using but not limited to digital manipulation with images, e.g., subtraction, division, calculation of derivative, integration, and the like.

The invention can include software for automatically assessing quality and performance of software tested during the trial.

Image quality can be defined as the absence of significant image artifacts, high spatial resolution, low noise level, and the like.

Performance can include but is not limited to computational efficiency (minimum computational operation steps to run through the software), CPU power, and the like. The fewer iterations, the more efficient is the software.

Quality of software is characterized by producing images with good quality, for example, good resolution and contrast, and the like, described above.

Performing a fast clinical trial of a new image reconstruction algorithm can be performed using the GRDBS and PIRIS systems.

Other embodiments of the invention are possible. For instance, the raw CT database can contain a module that converts raw data collected by scanners from different manufacturers in different formats into a universal format that can be easily read by all third-party software developers. The advantages of this module are manifold. The company that develops a conversion module can execute non-disclosure agreements with the CT manufacturers and get information about their raw data formats under the agreement. Thus, third-party developers will only be able to see the standard uniform format and the proprietary data formats of the CT manufacturers will not be compromised. Another advantage is that if the standard format is published and well-advertised, this will spur innovation since third-party developers will not have to worry about reading data in multiple formats from different CT manufacturers.

While most of image reconstruction is currently done in 3D, there can be some applications in which two-dimensional (2D) images are of interest. Thus, there can exist embodiments that deal with 2D and/or 3D image reconstruction. Similarly, imaging can be performed in (four dimensional) with time being the additional dimension, and so the database should also have capabilities for storing and processing of 4D data.

While normally one can expect a raw scan data transfer module to be located adjacent to at least one scanner, by utilizing an intranet of a hospital, one can get access to the raw data even if the transfer module is not located adjacent to any scanner.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A system for collecting and storing raw scan data of an object or objects and for performing raw scan data processing, image reconstruction and image interpretation, the system comprising:

a raw scan data transfer module for receiving raw scan data generated by at least one scanner following the completion of a scan of at least one object;

a raw scan data database system for receiving the raw scan data from the transfer module and for storing the raw scan;

a data processing, image reconstruction and image interpretation system for retrieving the raw scan data from the raw scan data database system, for providing image processing and image reconstruction from the raw scan data retrieved from the raw scan data database system to generate reconstructed images from stored scan data and for interpreting the reconstructed images, wherein the data processing, image reconstruction and image interpretation system further comprises;

software providing raw scan data processing and image reconstruction from raw scan data, software providing interpretation of the reconstructed images and updating of a computerized external data management picture archiving and communication system (PACS) with reconstructed volumes and the results of the interpretation; and a repository of image interpretation software for providing stored image interpretation software to the data processing, image reconstruction and image interpretation system, wherein the stored image interpretation software comprises a plurality of different image interpretation software programs.

2. The system of claim 1, wherein the raw scan data is generated by at least one scanner selected from at least one of: a computed tomography (CT) scanner, a magnetic resonance imaging (MRI) scanner, a positron emission tomography (PET) scanner, an ultrasound scanner, and scanners for other imaging modalities.

3. The system of claim 1, wherein the data processing, image reconstruction and image interpretation system is further configured for receiving at least one image reconstruction order for the raw scan data stored in the raw scan data database system, the image reconstruction order requesting the raw scan data to be processed and image reconstructed by the data processing, image reconstruction and image interpretation to provide additional reconstructed images.

4. The system of claim 3, wherein the image reconstruction order is generated based on analysis performed on stored raw scan data according to a recommended-by-the-system modified scan protocol.

5. The system of claim 1, wherein the raw scan data received from the scanner is compressed raw scan data, the system further comprising decompression software for decompressing the compressed raw scan data prior to storing the raw scan data in the raw scan data database system.

6. The system of claim 1, wherein the raw scan data database system includes:
  software providing raw scan data compression and decompression;
  a computer for storing raw scan data and image data.

7. The system of claim 3, wherein the data processing, image reconstruction and image interpretation system is further configured for transferring the reconstructed images to the computerized external data management picture archiving and communication systems (PACS).

8. The system of claim 6, wherein the computer for storing raw scan data and image data includes capabilities for storing raw scan data and image data in a local database or a centralized global database.

9. The system of claim 6, wherein the computer for storing raw scan data and image data includes capabilities for storing raw scan data and image data using cloud-based storage on the Internet.

10. The system of claim 1, wherein the raw scan data transfer module further comprises a digital information transfer medium to transfer the raw scan data from the at least one scanner to the raw scan data database system, the digital information transfer medium selected from at least one of: a WEB portal, the internet, a DVD (digital video disc), a CD (compact disc), a portable drives, and other software carrier transfer medium.

11. The system of claim 1, further comprising:
  a repository of software for providing stored software to the data processing, image reconstruction and image interpretation system, the repository of software including:
    a software development and trial system for qualifying software candidates for the repository of software, the software candidates including but not limited to raw scan data processing, image reconstruction and interpretation software; and
    testing procedures for performing software trials of the software candidates for the repository of software to determine if the software candidates satisfy the qualification requirements of the repository of software; and
  a Web-enabled portal to allow a developer of the software candidate to apply for a software trial and to transfer software modules based upon the software candidates to the repository of software if the software candidates satisfied qualification requirements of the repository of software.

12. The system of claim 11, wherein the software development and trial system includes:
  input and output data format standards required to be satisfied by the software candidates applying for the trial;
  phantom data sets for initial test runs performed by a software candidate,
  software retrieving a set of real patient or any object raw scan data from the raw scan data database to perform the trial;
  a queue trial system to manage a number of applicants associated with the software candidates, required computer power, and data storage volume;
  software for an automatic assessment of quality and performance of the software candidates tested during the trial.

13. The system of claim 11, wherein the software development and trial system includes a Web-enabled portal for uploading software candidates that have successfully passed through the software development and trial system to the repository of software, wherein the software candidates that have successfully passed become software programs available to any user worldwide via a Web-based system.

14. The system of claim 13, wherein a software program from the repository of software is available for use by a global data processing, image reconstruction, and image interpretation system, and is available to be uploaded to a scanner.

15. The system of claim 1, wherein the raw scan data received from the scanner is decompressed raw scan data, the system further comprising compression software for compressing the decompressed raw scan data prior to storing the raw scan data in the raw scan data database system.

16. The system of claim 1, further comprising, an Artificial Intelligence software system for interpreting the reconstructed images.

17. The system of claim 1, further comprising, an Artificial Intelligence software system for generating a new scan protocol and optimized data interpretation workflow based on an image reconstruction order and the available information on the at least one object scanned by the scanner or on similar objects in the raw scan data database system.

18. A system for collecting and storing raw scan data of an object or objects and for performing raw scan data processing, image reconstruction and image interpretation, the system comprising:
  a raw scan data transfer module for receiving raw scan data generated by at least one scanner following the completion of a scan of at least one object;
  a raw scan data database system for receiving the raw scan data from the transfer module and for storing the raw scan;
  a data processing, image reconstruction and image interpretation system for retrieving the raw scan data from the raw scan data database system and for providing data processing and image reconstruction from the raw scan data retrieved from the raw scan data database system to generate reconstructed images from stored scan data and for interpreting the reconstructed images;
  a repository of software for providing stored software to the data processing, image reconstruction and image interpretation system, the repository of software including:
    a software development and trial system for qualifying software candidates for the repository of software, the software candidates including but not limited to raw scan data processing, image reconstruction and interpretation software; and
    raw scan data from the raw scan data database system, testing procedures for performing software trials of the software candidates for the repository of software to determine if the software candidates satisfy the qualification requirements of the repository of software; and a Web-enabled portal to allow a developer of the software candidate to apply for a software trial and to transfer software modules based upon the software candidates to the repository of software if the software candidates satisfied qualification requirements of the repository of software.

19. A method for collecting and storing raw scan data of an object or objects and performing raw scan data processing, image reconstruction and image interpretation, the method comprising:
  receiving raw scan data generated by at least one scanner following the completion of a scan of at least one object;
  transferring the raw scan data to a raw scan data database system and storing the raw scan data in the raw scan data database system;
  retrieving the raw scan data from the raw scan data database system and generating reconstructed images from the stored raw scan data using a data processing, image reconstruction and image interpretation system, wherein the data processing, image reconstruction and image interpretation system further comprises, software providing raw scan data processing and image reconstruction from raw scan data, software providing interpretation of the reconstructed images and updating of a computerized external data management picture archiving and communication system (PACS) with reconstructed volumes and with the results of the interpretation and a repository of image interpretation software for providing stored image interpretation software to the data processing, image reconstruction and image interpretation system, wherein the stored image interpretation software comprises a plurality of different interpretation software programs.

20. The method of claim 19, wherein the raw scan data is generated by at least one scanner selected from at least one of: a computed tomography (CT) scanner, a magnetic resonance imaging (MRI) scanner, a positron emission tomography (PET) scanner, an ultrasound scanner, and scanners for other imaging modalities.

21. The method of claim 19, further comprising, receiving an image reconstruction order requesting the raw scan data to be processed and image reconstructed by the data processing, image reconstruction and image interpretation system prior to retrieving the raw scan data from the raw scan data database system and generating reconstructed images from the stored raw scan data using the data processing, image reconstruction and image interpretation system.

22. The method of claim 19, further comprising transferring the reconstructed images to the computerized external data management picture archiving and communication systems (PACS).

23. The method of claim 19, wherein the software providing image interpretation of the reconstructed images further comprises an Artificial Intelligence software system providing image interpretation of the reconstructed images.

24. The method of claim 23, wherein the Artificial Intelligence software system further provides image interpretation of the reconstructed images using one or more of, stored patient data and a scan protocol.

25. The method of claim 19, further comprising, generating, at an Artificial Intelligence software system, a new scan protocol and optimized data interpretation workflow based on an image reconstruction order and the available information on the at least one object scanned by the scanner or on similar objects in the raw scan data database system.

26. A system for collecting and storing raw scan data of an object or objects and for performing raw scan data processing and image reconstruction, the system comprising:
  a raw scan data transfer module for receiving raw scan data generated by at least one scanner following the completion of a scan of at least one object;
  a raw scan data database system for receiving the raw scan data from the transfer module and for storing the raw scan;
  a data processing and image reconstruction system for retrieving the raw scan data from the raw scan data database system and for providing data processing and image reconstruction from the raw scan data retrieved from the raw scan data database system to generate reconstructed images;
  a repository of image reconstruction software for providing stored image reconstruction software to the data processing and image reconstruction system, wherein the stored image reconstruction software comprises a plurality of different image reconstruction software programs.

27. A method for collecting and storing raw scan data of an object or objects and performing raw scan data processing and image reconstruction, the method comprising:
  receiving raw scan data generated by at least one scanner following the completion of a scan of at least one object;
  transferring the raw scan data to a raw scan data database system and storing the raw scan data in the raw scan data database system;
  retrieving the raw scan data from the raw scan data database system and generating reconstructed images from the stored raw scan data using a data processing and image reconstruction system, wherein the data processing and image reconstruction system further comprises, software providing raw scan data processing and image reconstruction from raw scan data and a repository of image reconstruction software for providing stored image reconstruction software to the data processing and image reconstruction system, wherein the stored image reconstruction software comprises a plurality of different image reconstruction software programs.

* * * * *